US00PP35118P2

(12) United States Plant Patent
Chen et al.

(10) Patent No.: US PP35,118 P2
(45) Date of Patent: Apr. 25, 2023

(54) PEACH TREE NAMED 'MAY JOY'

(50) Latin Name: ***Prunus persica* (L.) Batsch.**
Varietal Denomination: May Joy

(71) Applicant: The United States of America, as represented by the Secretary of Agriculture, Washington, DC (US)

(72) Inventors: Chunxian Chen, Byron, GA (US); William R. Okie, Augusta, GA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 17/880,414

(22) Filed: Aug. 3, 2022

(51) Int. Cl.
*A01H 5/08* (2018.01)
*A01H 6/74* (2018.01)

(52) U.S. Cl.
USPC ..... Plt./197
CPC ..... *A01H 6/7463* (2018.05)

(58) Field of Classification Search
USPC ..... Plt./197
CPC ..... A01H 6/7463
See application file for complete search history.

*Primary Examiner* — Anne Marie Grunberg
(74) *Attorney, Agent, or Firm* — John D. Fado; Maria Restrepo-Hartwig

(57) ABSTRACT

A new and distinct cultivar of peach tree, denominated 'May Joy', has clingstone, melting, yellow-flesh fruit with normal acidity and pleasant eating quality. The fruit typically are round, ripen approximately 1-2 weeks before 'Flavorich' (syn. 'Rich May') and 2-3 weeks before 'Carored' in early to mid-May in Byron, Ga., and have a high percentage of red blush with an attractive yellow ground color. The tree is moderately vigorous and semi-spreading in growth habit, has self-fertile showy pink flowers, and regularly bears crops in absence of severe spring frost. This cultivar has a winter chilling requirement estimated at approximately 650 chill hours and is suited for medium to high chill areas.

4 Drawing Sheets

Latin name of the genus and species of the plant claimed: 'May Joy' is a peach tree that is a *Prunus persica* (L.) Batsch.

Cultivar denomination: The new peach tree is of the cultivar denominated 'May Joy'.

BACKGROUND OF THE NEW PLANT

The present invention relates to a new and distinct peach cultivar designated 'May Joy', botanically known as *Prunus persica* (L.) Batsch, and tested as BY02P2562 obtained from a hand-pollinated cross between 'Scarletprince' (unpatented, the seed parent) and Y153-53 (an advanced selection, unpatented, the pollen parent) yellow peaches. Fruit of 'May Joy' ripen approximately 54 days before 'Scarletprince' and 10 days after Y153-53. This new peach tree has a chilling requirement of ~650 hours and ripens in early to mid-May in Byron, Ga. 'May Joy' is adapted to a Southeastern subtropical climate with moderate chill in winters and worthy of commercial production trials for the fresh fruit market. Clonal plants were asexually propagated from the original 'May Joy' tree by grafting on 'Guardian'® (unpatented) peach seedling rootstocks in Byron, Ga. These asexually propagated plants, along with all characteristics of the tree and the fruit, remained true-to-type to the original 'May Joy' tree. There are no known effects of the standard rootstock on the scion cultivar characteristics.

'May Joy' produces clingstone, melting, yellow-flesh fruit with normal acidity, pleasant eating quality, and attractive blush, which ripens in early to mid-May in Byron, Ga. 'May Joy' is a promising candidate for commercial success in the early harvest season in that it produces attractive early-season fruit.

Byron, Ga. is under a subtropical climate. Winters are short, mild and with little snow; summers are long, hot and humid. The average January low temperature is about 1.2° Celsius and the average July high temperature is about 33.2° Celsius. The hours with temperatures below 7.2° Celsius (45.0° Fahrenheit) vary often between 600 and 1200 hours per year. There are about 67 rainy days per year. Average annual precipitation (rainfall) is 1182.9 millimeters (46.6 inches) with great monthly and yearly variabilities and frequent thunderstorms in summers.

SUMMARY OF THE INVENTION

The new and distinct cultivar 'May Joy' peach tree blooms late February, approximately with (or slightly after) 'Junegold' (unpatented) and 'Springprince' (unpatented) and a few days before 'GaLa' (unpatented) and 'Sunland' (unpatented) peach trees in Byron, Ga. The estimated chilling requirement, based on bloom time, is approximately 650 chill hours. The blooming period and the blooming date are dependent on climatic conditions. The flower anthers are yellow, and leaf glands are reniform, characteristic of many standard peach cultivars.

The first fruit of 'May Joy' ripen generally in early to mid-May in Byron, Ga., approximately a week before 'Flavorich' (syn. 'Rich May', patented: U.S. Plant Pat. No. 7,432) and 2-3 weeks before 'Carored' (unpatented). 'May Joy' trees are vigorous and productive, and fruit size moderately well if not overcropped. 'May Joy' fruit have melting texture, pleasant eating quality, and high blush coverage (approximately 80-90% red skin). The potential for commercial production of fresh 'May Joy' fruit is high, due to its attractive blush and very early harvest at Byron, Ga.

BRIEF DESCRIPTION OF THE PHOTOGRAPHS

The accompanying drawings are color photographs that are taken at Byron, Ga. and that are as nearly true as it is reasonably possible to make in a color illustration of this type:

FIG. 1 is a color photograph that shows a close view of typical ripening fruits of the new cultivar 'May Joy'.

FIG. 2 is a color photograph that shows the shape, exterior and flesh colors with six specimens of 'May Joy' fruit arranged in four columns: suture and back side view (top and bottom in column 1), blossom and stem end view (2), longitudinal cross sections (3), and latitudinal cross sections (4). The cross sections are deliberately off the suture-back line and the equator of the fruit because of the clingstone that prevents equal halves of the fruit from being neatly and intactly separated by hand twisting force.

Figure 1:
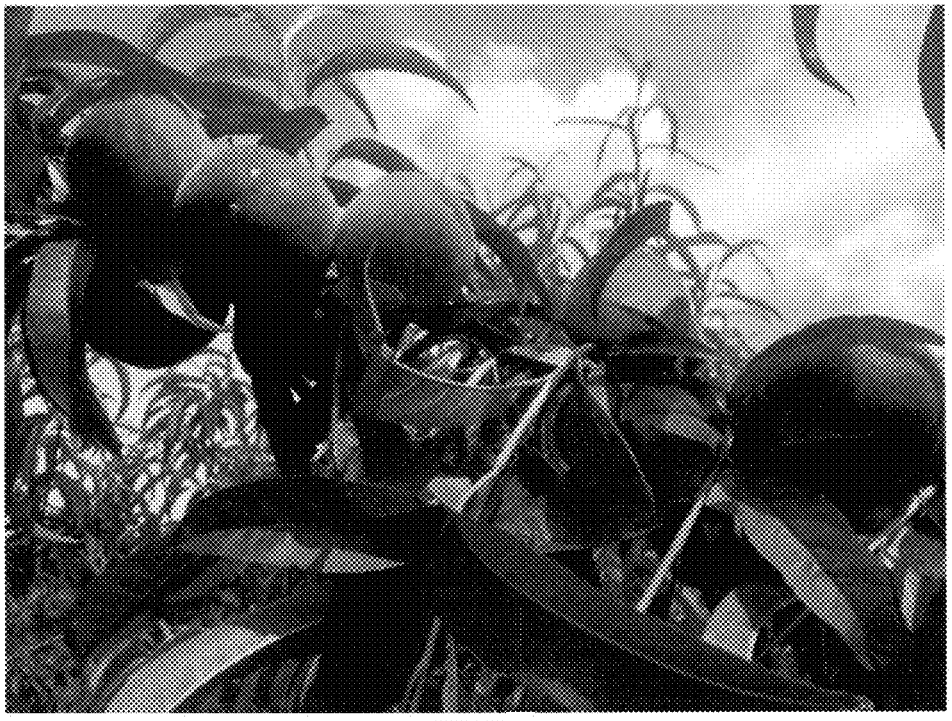
Figure 2:
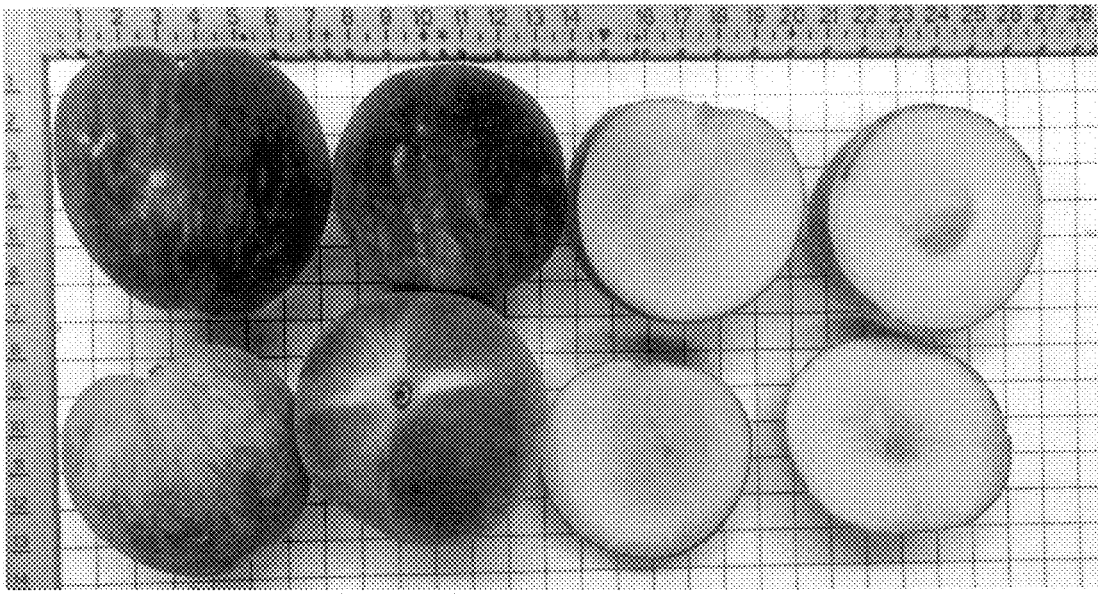
Figure 3:
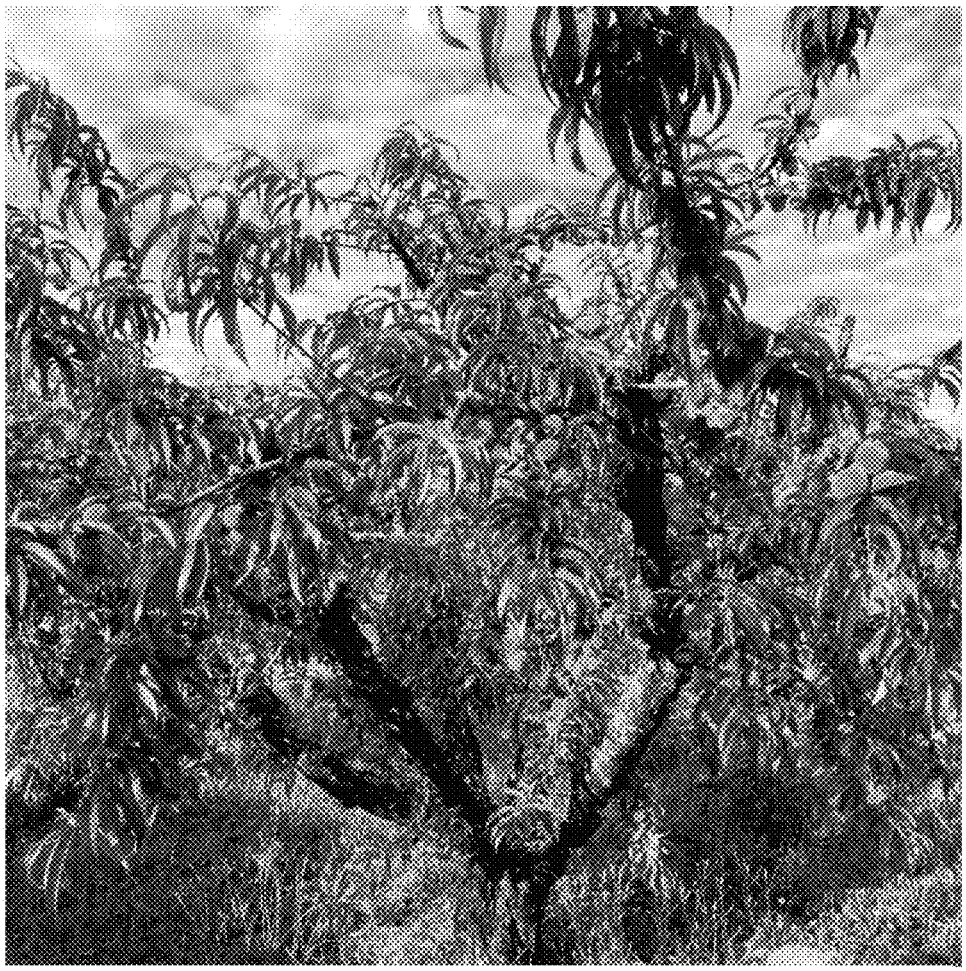
FIG. 3 is a color photograph that shows the typical semi-spreading architecture of a 12-year-old tree of the new cultivar 'May Joy'.
Figure 4:
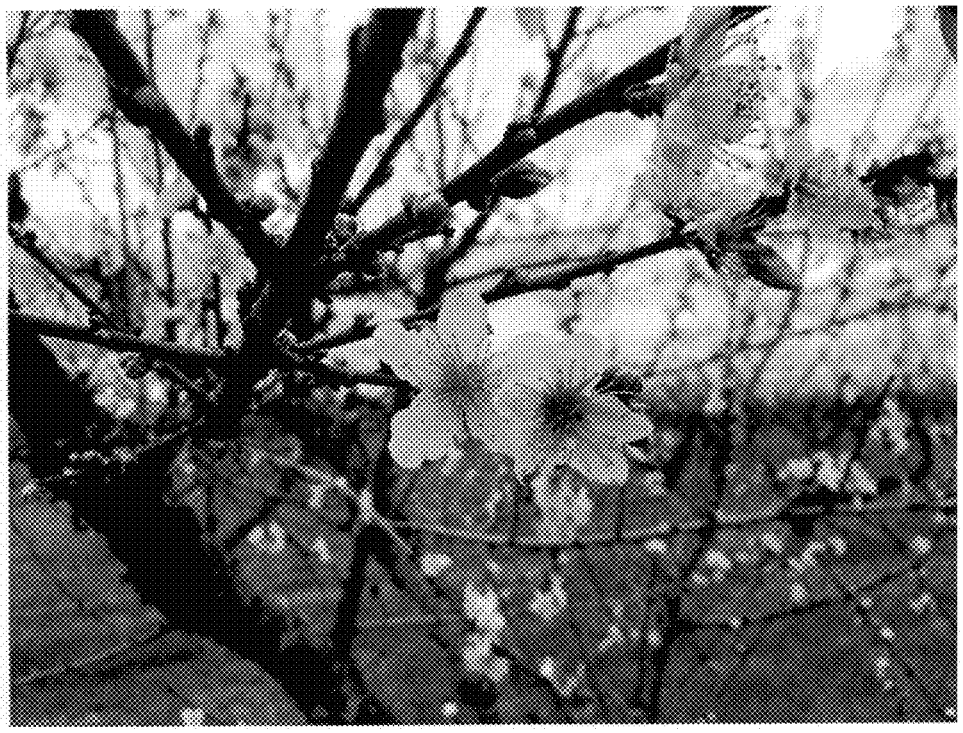
FIG. 4 is a color photograph that shows typical showy flowers of 'May Joy'.

Due to photographical light, chemical development, processing, and printing, the leaves and fruit depicted in these photographs may or may not be accurate when compared to the actual botanical specimen.

DETAILED BOTANICAL DESCRIPTION

The tree, flowers, and fruit may vary in slight detail due to variations in climatic conditions, cultural practices, growing seasons, development stages and soil types. Referring more specifically to the detailed botanical description of this new and distinct cultivar of yellow peach tree, the following was observed on 12-year-old trees of the cultivar grafted on 'Guardian'® rootstock under the ecological conditions prevailing at the orchards located at the town of Byron, Ga., USA. All major color code designations are by reference to The Royal Horticultural Society (R.H.S.) Colour Chart (Fourth Edition).

Tree:

*Size*.—Generally considered large when trained to an open vase form. The average height and width of 12-year-old trees are 3.4 meters and 4.3 meters, respectively, including current season shoots.

*Spread*.—Grown to a vase shape with summer and winter pruning to keep the tree open to get strong fruiting wood in the lower center.

*Vigor*.—Considered moderately vigorous. Trees respond typically to irrigation and fertilization in the orchards at Byron, Ga.

*Productivity*.—Productive most years. Fruit set is reduced by thinning to develop the remaining fruit into desired market size. The fruit number varies with the prevailing climatic conditions and cultural practices.

*Bearer*.—Regular most years. The fruit is distributed homogenously on both short and long shoots and must be thinned to avoid limb breakage and obtain large fruit size.

*Form*.—Semi-spreading, but easily pruned to vase shape.

*Density*.—Considered dense. Pruning is required to open the tree center to promote sunlight entrance for enhancing fruit color and sugar.

*Hardiness*.—Hardy with respect to typical Byron, Ga. winters.

*Chilling requirement*.—Estimated endodormancy chilling requirement is approximately 650 chill hours based on time of bloom and leafing in relation to standard varieties.

*Vegetative bud break time*.—Late February, approximately 1 week after bloom depending on winter chilling and amount of warm weather.

Trunk:

*Size*.—Approximately 27.8 centimeters in diameter and at a height of approximately 30.0 centimeters on the 12-year-old trees at Byron, Ga.

*Bark texture*.—Generally smooth, but changes to light shaggy as tree ages.

*Bark color*.—RHS Greyed Group 201D. Bark crack's color is RHS Black Group 202A.

*Lenticels*.—Moderately low number, approximately 1 per square centimeter of surface area of trunk; and the average lenticel length and width of lenticels are approximately 5.9 millimeters and 2.0 millimeters, respectively.

*Lenticel color*.—RHS White Group 155B.

Branches:

*Size*.—Average as compared to other peach cultivars. Strong growth of scaffold branches. The current season mature fruiting branches have a diameter from 9.2 to 14.4 millimeters, and the average diameter is 11.37 millimeters. Tree growth and structure permits easier and faster winter pruning.

*Surface texture*.—Relatively smooth, numerous lenticels but smaller size than found on trunk and old scaffolds. Roughness increases with age.

*Crotch angles*.—Acute, within the normal range of standard cultivars for a semi-spreading tree after proper summer and winter pruning.

*Internode length*.—Approximately 2.2 to 3.3 centimeters with the average of 2.8 centimeters.

*Color of current season shoots*.—RHS Red-Purple Group 58D at the upper part (sunny side) of the shoots and RHS Yellow-Green Group 147D at the lower part (shady side) of the shoots.

*Color of mature branches*.—RHS Greyed-White Group 156C at the upper part (sunny side) of the shoots and RHS Greyed-Green Group 197A at the lower part (shady side) of the shoots.

Leaves:

*Size*.—Considered medium to large for the species.

*Length*.—Approximately 14.2 to 19.3 centimeters with the average of 16.8 centimeters, not including the petiole.

*Width*.—Approximately 3.3 to 4.3 centimeters with the average of 3.7 centimeters.

*Thickness*.—Regular and average for commercial cultivars, approximately 0.021 to 0.07 millimeters with the average of 0.05 millimeter, not noticeably unusual.

*Form*.—Lanceolate with serrulate margins.

*Apex*.—Acute.

*Margin*.—Serrulate.

*Base*.—Acute.

*Surface*.—Upper, glabrous; Lower, medium to large veins that are pinnately netted.

*Color*.—Regular green, slightly different in seasons. In early shoot growth, upper and lower leaf surfaces are RHS Green Group 137B and Yellow-Green Group 147B, respectively. In late season, upper leaf surface is RHS Green Group 147B and lower surface is RHS Yellow-Green Group 147C. Leaf vein is RHS Red-Purple Group 59B.

*Glands*.—Reniform. Usually 2 on lower leaf blade and 2 on petioles. Color is RHS Yellow-Green Group 139D. Approximately 1.3 to 1.8 millimeters long with the average of 1.5 millimeters, approximately 0.5 to 1.0 millimeters wide with the average of 0.8 millimeters.

*Petiole*.—Approximately 8.2 to 12.5 millimeters length with the average of 10.1 millimeters, approximately 1.4 to 2.0 millimeters diameter with the average of 1.77 millimeters. Color is RHS Yellow-Green Group 146B.

*Stipules*.—Medium, equal to most commercial peach cultivars, present on early shoot growth. Color at full size is RHS Greyed-Orange Group 172A before abscising.

*Leaf blade incisions*.—Serrulate.

*Arrangement*.—Alternate.

*Cross-section shape*.—Leaf blade forms a vee of about 130 degrees.

Flowers:

*Flower buds*.—The form of flowers buds changes as blooming approaches, with variable dimensions. They are conic at pre-floral stage and approximately 4.0 to 5.9 millimeters long with the average of 4.7 millimeters and 2.4 to 3.2 millimeters wide with the average of 2.7 millimeters. The bud color in mid-winter is RHS Greyed-Green Group 188B. Most buds set fruit in absence of spring frost.

*Hardiness*.—Hardy with respect to Byron, Ga. winters.

*Date of bloom*.—late February depending on winter chill hours and amount of warm weather.

*Blooming time*.—Considered early in bloom relative to other commercial peaches in central GA. Typically blooms with or slightly after 'Springprince' and 'Junegold' (650 chill hours) and a few days before 'GaLa' and 'Sunland' (750 chill hours).

*Duration of bloom*.—Approximately 6 to 14 days. This characteristic varies significantly with chill hours accumulated in winter as well as temperatures during bloom.

*Bloom quantity*.—Generally abundant, with a good distribution.

*Flower bud frequency*.—Generally two flower buds per node, but occasionally three.

*Fragrance*.—Undetectable or faint floral scent.

*Type*.—Showy.

*Shape*.—Rosette.

*Fertility*.—Self-fertile.

*Size*.—Approximately 31.5 to 38.4 millimeters in diameter at full bloom, with the average of 34.9 millimeters.

*Petal*.—Size: Generally considered large. Length: approximately 14.5 to 18.3 millimeters with the average of 16.3 millimeters. Width: approximately 9.2 to 13.5 millimeters with the average of 11.5 millimeters. Form: generally round-shaped. Count: almost always five. Arrangement: usually free, sometimes touching. Texture: smooth, soft and glabrous. Color: RHS Red-Purple Group 63D and 62C in the upper and lower surface, respectively. Margins: generally slightly undulating. Apex: generally round and curved-shaped.

*Pedicel*.—Length: approximately 1.1 to 2.1 millimeters with the average of 1.52 millimeters. Diameter: approximately 2.3 to 2.9 millimeters with the average of 2.6 millimeters.

*Calyx cup*.—Diameter: approximately 12.9 to 15.1 millimeters with the average of 13.9 millimeters. Color: RHS Yellow-Green Group 146B at the interior surface and Greyed Red Group 178A at the exterior surface.

*Sepals*.—Number: generally five sepals. Length: approximately 4.5 to 5.9 millimeters with the average of 5.3 millimeters. Width: approximately 4.1 to 4.9 millimeters with the average of 4.5 millimeters. Color: RHS Red-Purple Group 59B.

*Stamen number*.—Approximately 28 to 37 stamens per flower with the average of 31.7.

*Anthers*.—Color: RHS Yellow-Orange Group 16A at opening. Anthers arrayed above petals.

*Pollens*.—Generally abundant and approximately RHS Yellow-Orange Group 18A.

*Filaments*.—Length at opening: approximately 10.5 to 15.8 millimeters with the average of 12.5 millimeters. Color: RHS Red Group 36C.

*Pistil*.—Number: Usually one. Length: approximately 7.9 to 9.3 millimeters with the average of 8.6 millimeters. Color: RHS Yellow-Green Group 150C. Stigma slightly below than anthers.

Fruit:

*Maturity when described*.—Moderately firm when ripe for commercial picking.

*Date of harvest*.—Vary slightly with the prevailing climatic conditions. Harvest in 2019 at Byron, Ga. was May 8 until May 13.

*Size*.—Generally uniform, medium size. Weight: approximately 101.7 to 157.5 grams with the average of 121.6 grams. Equatorial diameter: approximately 58.7 to 69.0 millimeters with the average of 63.6 millimeters. Polar diameter (from stem to distal end): at the suture-back orientation approximately 56.6 to 67.2 millimeters with the average of 60.5 millimeters, and at the cheek-cheek orientation approximately 58.2 to 66.5 millimeters with the average of 61.7 millimeters. This characteristic highly depends on fruit number per tree, soil type, climatic conditions, and cultural practices, and therefore is not particularly distinctive of the cultivar.

*Peduncle*.—Length: approximately 3.6 to 4.7 millimeters with the average of 4.3 millimeters. Width: approximately 2.7 to 3.3 millimeters with the average of 3.0 millimeters. Color: RHS Green Group 142D.

*Longitudinal section form*.—Round, slightly squat.

*Transverse section through diameter*.—Generally round.

*Suture*.—Very slight indentation.

*Ventral surface*.—Generally round, smooth.

*Shape of fruit base*.—Round to slightly cordate.

*Apex*.—Round-Ovate, occasionally with small cuspidate tip.

*Crater at stem attachment*.—Flaring oval to the suture. Width at top (cheek to cheek): approximately 13.1 to 22.2 millimeters with the average of 17.4 millimeters. Width at top (suture to back): approximately 21.3 to 32.2 millimeters with the average of 26.8 millimeters. Width at bottom (pedicel attachment): approximately 2.6 to 4.2 millimeters with the average of 3.3 millimeters. Depth: approximately 6.1 to 9.6 millimeters with the average of 7.5 millimeters.

*Skin*.—Thickness: generally medium in comparison to commercial peach cultivars. Texture: generally typical of commercial peach cultivars. Tenacity: Tenacious. Color: RHS Greyed-Purple 187B, approximately 85% to 95% of skin. Fruit exposed to sunlight likely have a higher degree of enhanced skin color. Ground color: RHS Yellow Group 4C. Tendency to crack: None observed. Taste: No astringency observed. Epidermis: Typical short pubescence.

*Flesh*.—Ripens: evenly within each fruit. Texture: smooth, melting, and juicy when fully ripe. Fibers: many tender fibers through flesh. Aroma: slight and typical of commercial peach varieties. Eating quality: pleasant flavor with typical acidity for fresh market. Soluble solid content: 9.3 to 13.1° Brix, with an average of 11.45 of ten fruits harvested on May 13, 2019. pH values: 3.4 to 3.7, with an average of 3.56 of ten fruits harvested on May 13, 2019. Color: RHS Orange Group 6B. Color of red flecks within flesh: RHS Red Group 42B. Color of flesh at pit: RHS Yellow Group 6B. Browning by oxidation: none observed on tree ripe fruit beginning to soften. Amygdalin: none detected.

Stone:

*Type*.—Clingstone.

*Size*.—Generally medium large. The stone size varies upon the tree vigor, crop load and prevailing growing conditions. Length: approximately 26.9 to 29.9 millimeters with the average of 28.3 millimeters. Width: approximately 22.9 to 26.3 millimeters with the average of 24.8 millimeters. Diameter (thickness at the cheek-cheek orientation): approximately 18.8 to 20.3 millimeters with the average of 19.5 millimeters.

*Wall thickness*.—Approximately 5.8 to 6.9 millimeters with the average of 6.5 millimeters at the cheek.

*Color*.—RHS Orange-White Group 159A when flesh is freshly cut.

*Form*.—Oblong.

*Base*.—Straight.

*Apex*.—Obtuse with some seeds having a cuspidate tip.

*Sides*.—Nearly equal.

*Surface*.—Generally furrowed toward ventral edge, lighted pitted from base to apex.

*Tendency to split*.—Split pits observed some years.

*Kernel*.—Likely not viable, 8 out 10 seeds still white upon removal from fruit at harvest. Taste: bitter. Size: Considered medium large. Length: approximately 13.4 to 16.4 millimeters with the average of 15.1 millimeters. Width: approximately 9.2 to 11.4 millimeters with the average of 10.3 millimeters. Thickness: approximately 4.5 to 5.9 millimeters with the average of 5.3 millimeters. Form: obtuse base with acute tip and overall ovate shape. Color: RHS Yellow Group 4D.

Use of the fruit: Fresh, dessert.

Keeping quality: Good after about 1-2 weeks at approximately 2 to 8 degrees Celsius and with little bruising or scarring appearing on skin. Soften at room temperature.

Shipping quality: Considered acceptable. The fruit showed little bruising of the flesh or skin damage or internal breakdown of flesh under refrigeration at approximately 2 to 8 degrees Celsius indicates fruit should be highly acceptable for shipping.

Resistance to disease: Moderate resistance to bacterial spot incited by *Xanthomonas campestris* pv. *pruni*. No unusual resistance or susceptibility to insects and diseases was noted.

We claim:

1. A new and distinct cultivar of peach tree named 'May Joy' as illustrated and described, characterized by a moderate chilling requirement, an early maturity, and attractive ripe fruit with a high coverage of red blush, melting texture, yellow flesh, normal acidity, pleasant eating quality, and clingstone.

* * * * *